US005632840A

United States Patent [19]
Campbell

[11] Patent Number: 5,632,840
[45] Date of Patent: May 27, 1997

[54] METHOD OF MAKING METAL REINFORCED POLYMER STENT

[75] Inventor: Patrick K. Campbell, Georgetown, Mass.

[73] Assignee: Advanced Cardiovascular System, Inc., Santa Clara, Calif.

[21] Appl. No.: 467,706

[22] Filed: Jun. 6, 1995

Related U.S. Application Data

[62] Division of Ser. No. 310,579, Sep. 22, 1994.

[51] Int. Cl.⁶ .............................. B32B 31/04; B32B 31/18
[52] U.S. Cl. .......................... 156/196; 156/218; 156/252; 156/267; 156/308.2; 623/1
[58] Field of Search .................................. 623/1, 2, 11, 12, 623/13, 900; 156/196, 211, 218, 221, 223, 252, 253, 267, 308.2

[56] References Cited

U.S. PATENT DOCUMENTS

| | | |
|---|---|---|
| 4,441,215 | 4/1984 | Kaster . |
| 4,573,242 | 3/1986 | Lankton et al. ............ 24/30.5 P |
| 4,640,320 | 2/1987 | Avison et al. ............... 24/16 PB |
| 4,669,474 | 6/1987 | Barrows . |
| 4,718,907 | 1/1988 | Karwoski et al. . |
| 4,752,054 | 6/1988 | Jonsson ...................... 24/16 PB |
| 4,762,128 | 8/1988 | Rosenbluth .................... 128/343 |
| 4,776,337 | 10/1988 | Palmaz . |
| 4,813,416 | 3/1989 | Pollak et al. .............. 24/16 PB |
| 4,816,339 | 3/1989 | Tu et al. . |
| 4,866,816 | 9/1989 | Caveney ................... 24/30.5 P |
| 4,877,030 | 10/1989 | Beck et al. . |
| 4,878,906 | 11/1989 | Lindemann et al. . |
| 4,879,135 | 11/1989 | Greco et al. . |
| 4,902,290 | 2/1990 | Fleckenstein et al. . |
| 4,950,285 | 8/1990 | Wilk ............................ 24/16 PB |
| 4,986,831 | 1/1991 | King et al. . |
| 5,007,926 | 4/1991 | Derbyshire ....................... 623/1 |
| 5,059,166 | 10/1991 | Fischell et al. . |
| 5,059,211 | 10/1991 | Stack et al. . |
| 5,064,435 | 11/1991 | Porter . |
| 5,078,736 | 1/1992 | Behl . |
| 5,084,065 | 1/1992 | Weldon et al. . |
| 5,100,429 | 3/1992 | Sinofsky et al. . |
| 5,104,403 | 4/1992 | Brotzu et al. . |
| 5,116,360 | 5/1992 | Pinchuk et al. . |
| 5,123,917 | 6/1992 | Lee . |
| 5,147,385 | 9/1992 | Beck et al. . |
| 5,156,620 | 10/1992 | Pigott . |
| 5,156,623 | 10/1992 | Hakamatsuka et al. . |
| 5,158,548 | 10/1992 | Lau et al. . |
| 5,163,951 | 11/1992 | Pinchuk et al. . |
| 5,180,366 | 1/1993 | Woods . |
| 5,192,307 | 3/1993 | Wall .............................. 623/1 |
| 5,192,310 | 3/1993 | Herweck et al. . |
| 5,192,311 | 3/1993 | King et al. . |
| 5,195,984 | 3/1993 | Schatz ........................... 606/194 |
| 5,197,977 | 3/1993 | Hoffman, Jr. et al. . |
| 5,234,456 | 8/1993 | Silvestrini . |
| 5,234,457 | 8/1993 | Andersen . |
| 5,258,020 | 11/1993 | Froix . |
| 5,279,594 | 1/1994 | Jackson . |
| 5,282,823 | 2/1994 | Schwartz et al. . |
| 5,289,831 | 3/1994 | Bosley . |
| 5,290,271 | 3/1994 | Jernberg . |
| 5,304,220 | 4/1994 | Maginot . |
| 5,306,286 | 4/1994 | Stack et al. . |

(List continued on next page.)

FOREIGN PATENT DOCUMENTS

| | | | |
|---|---|---|---|
| 364787 | 4/1990 | European Pat. Off. ................ 623/1 |
| 0382014 | 8/1990 | European Pat. Off. ................ 623/1 |
| WO94/21196 | 9/1994 | WIPO ..................................... 623/1 |

*Primary Examiner*—Steven D. Maki
*Attorney, Agent, or Firm*—Fulwider Patton Lee & Utecht, LLP

[57] ABSTRACT

The metal reinforced polymer stent for use in blood vessels is formed of a thin planar sheet of metal, and is laminated on at least one side with a thin film of a polymer capable of absorbing and releasing therapeutic drugs. The thin planar sheet of metal is formed as a sheet and cut in a shape that can be used as a stent, the ends of which can be joined in a contractible, expandable loop.

5 Claims, 2 Drawing Sheets

U.S. PATENT DOCUMENTS

| | | |
|---|---|---|
| 5,312,339 | 5/1994 | Boussignac et al. . |
| 5,330,500 | 7/1994 | Song . |
| 5,334,201 | 8/1994 | Cowan . |
| 5,337,503 | 8/1994 | Goby .................................. 24/30.5 PB |
| 5,342,348 | 8/1994 | Kaplan . |
| 5,342,621 | 8/1994 | Eury ................................... 424/423 |
| 5,344,426 | 9/1994 | Lau et al. ................................. 623/1 |
| 5,344,444 | 9/1994 | Glastra . |
| 5,354,329 | 10/1994 | Whalen . |
| 5,356,423 | 10/1994 | Tihon et al. . |
| 5,356,433 | 10/1994 | Rowland et al. . |
| 5,383,928 | 1/1995 | Scott et al. .................................. 623/1 |
| 5,441,515 | 8/1995 | Khosravi et al. ........................... 623/1 |
| 5,443,458 | 8/1995 | Eury ......................................... 623/12 |
| 5,443,500 | 8/1995 | Sigwart ..................................... 623/12 |
| 5,449,382 | 9/1995 | Dayton ....................................... 623/1 |

METHOD OF MAKING METAL REINFORCED POLYMER STENT

This is a division, of application Ser. No. 08/310,579, filed Sep. 22, 1994.

BACKGROUND OF THE INVENTION

1. Field of the Invention

This invention relates generally to expandable intraluminal vascular grafts, generally referred to as stents, and more particularly concerns metal stents coated with a polymer capable of carrying and releasing therapeutic drugs.

2. Description of Related Art

Stents used to maintain patency of vessels in the body are typically implanted within a vessel in a contracted state, and are expanded when in place in the vessel to allow fluid to flow through the vessel and the stent. Such a stent can typically be moved along a guide wire previously placed in the vessel, and expanded by inflation of a balloon within the stent. Deflation of the balloon and removal of the guide wire leaves the stent in place in the vessel, locked in an expanded state. While stents are typically formed from biocompatible metals such as stainless steel, tantalum or gold, to provide sufficient strength to function as a stent, and with a minimal thickness so as to minimize blood flow blockage, such stents can cause complications such as thrombosis, and can cause neointimal hyperplasia, such as by inducement of smooth muscle cell proliferation at the site of implantation of the stent. Such stents typically also do not provide for the delivery of localized therapeutic pharmacological treatment of a blood vessel at the location being treated with the stent, which can be useful for overcoming such problems.

Polymeric materials capable of absorbing and releasing therapeutic drugs do not generally have sufficient strength to function as a stent to maintain luminal patency. It would therefore be desirable to form a stent of a combination of materials that provide sufficient radial strength to serve as a stent, and are capable of absorbing therapeutic drugs and releasing them at a predictable rate for an ascertainable period of time in a blood vessel. The present invention meets these needs.

SUMMARY OF THE INVENTION

Briefly, and in general terms, the present invention provides for a stent with a thin metal reinforcement coated with a polymer capable of carrying and releasing therapeutic drugs. The thin metal reinforcement provides the structural strength required for maintaining the patency of the vessel in which the stent is placed, and the polymer coating provides the capacity for carrying and releasing therapeutic drugs at the location of the stent, without significantly increasing the thickness of the stent. The stent of the invention is easily manufactured in sheet form, and rolled on a mandrel preparatory to implantation as a stent. The polymer coating of the stent can be completely degradable and absorbable within the body, and can be capable of delivering therapeutic drugs locally within a blood vessel. The coating can be multi-layered to allow for retention and delivery of selected drugs within an affected blood vessel upon implantation. Such multi-layering of the coating of the stent allows a plurality of different drug containing materials to be combined in a single stent. Depending upon the construction and lamination of the stent, drugs can be released simultaneously or sequentially, on the exterior surface of the stent to a blood vessel wall, and directly into the bloodstream, as desired.

The invention accordingly provides for a stent with a thin metal reinforcement member that is coated on at least one side with a thin film of a material capable of drug delivery. The metal reinforced, polymer coated stent is preferably formed as a sheet and cut in a shape that can be used as a stent, such as a "belt-buckle" type shape with head and tail portions that can be joined in an expandable loop that will lock in an expanded configuration. The stent is preferably cut in such a shape from a thin sheet of metal to have head and tail ends and a main body portion between the head and tail ends. The inner metal reinforcement structure is preferably formed from a thin sheet of metal, such as stainless steel, although other metals such as platinum-iridium alloy, molybdenum-rhenium alloy, tantalum, gold, combinations thereof and other similar materials that may also be suitable.

The head end of the stent preferably includes a slot for receipt of the tail end, so that the tail end and main body portion are insertable through the slot so as to form a cylindrical loop. The slot at the head end preferably includes a plurality of teeth adapted to cooperatively engage a plurality of holes in the tail end and main body portion for retaining the tail end when inserted in the slot, so that the stent can be placed in a blood vessel in a contracted cylindrical loop shape, urged into an expanded configuration, such as by an inflation balloon, and locked in the expanded configuration by the interlocking of the teeth in the slot with the holes in the tail and main body portion.

The polymer used for coating the metal reinforcement member is preferably a biodegradable, bioabsorbable polymer selected from the group consisting of poly-DL-lactic acid (DL-PLA) and poly-L-lactic acid (L-PLA), although other biodegradable polymers, such as polyorthoesters, polyiminocarbonates, aliphatic polycarbonates, and polyphosphazenes may also be suitable, and other non-degradable polymers capable of carrying and delivering therapeutic drugs may also be suitable. The thin polymeric films with which the stent is coated are preferably first intermixed with the drug or drugs to be delivered, and then are typically solvent cast or laminated to the surface of the metal stent.

The invention also provides for a method of making a stent having a metal reinforcement member coated with a polymer capable of carrying and releasing therapeutic drugs, for use in blood vessels. In the preferred method, a plurality of metal reinforcement structures are first cut, preferably with a laser, from a thin sheet of metal in a locking configuration, with a head end containing a slot with teeth for receiving and retaining the perforated tail and main body portions, and with the individual reinforcement structures connected, such as directly at the head end, and by tabs at the tail ends. The metal reinforcement structures can also be cut by other methods known in the art, such as by chemical etching, or stamping. The connecting tabs at the tail ends are provided and retained during a majority of the manufacturing process to help maintain the proper orientation of the metal reinforcement structures. The metal reinforcement structures are then preferably laminated with polymer films on each side of the stent, with at least one coating of a polymer film, although the polymer coating can also be applied by casting the polymer onto the metal reinforcement structures. Alternatively, the metal reinforcement structure can also be coated on one side, if desired. Once the metal reinforcement members are coated with the polymer, excess polymer in the orifices of the tail and main body portions and extending beyond the perimeter of the inner reinforcement members is removed, preferably by laser cutting, although the excess polymer can also be removed by stamping. The teeth in the slotted portion of the head end of the joined stent structures are then preferably bent to extend about 45° out of the plane of the stent, preparatory to insertion of the tail and main body portions in the slotted head, the tabs joining the individual stent structures are then cut and removed, the tail ends are inserted in the slots, and the stents are rolled onto a mandrel into a coiled shape ready for expansion and implantation.

These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
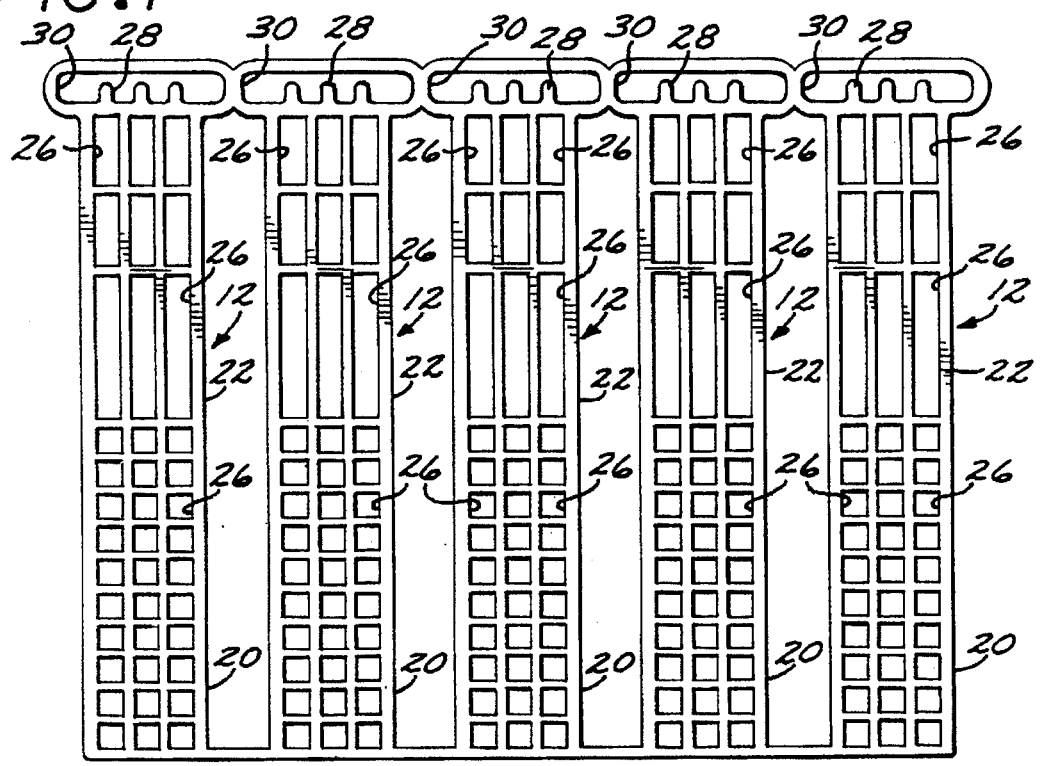
FIG. 1 is a top plan view of a plurality of the metal reinforcement members of the metal reinforced polymer stent of the invention.
Figure 2:
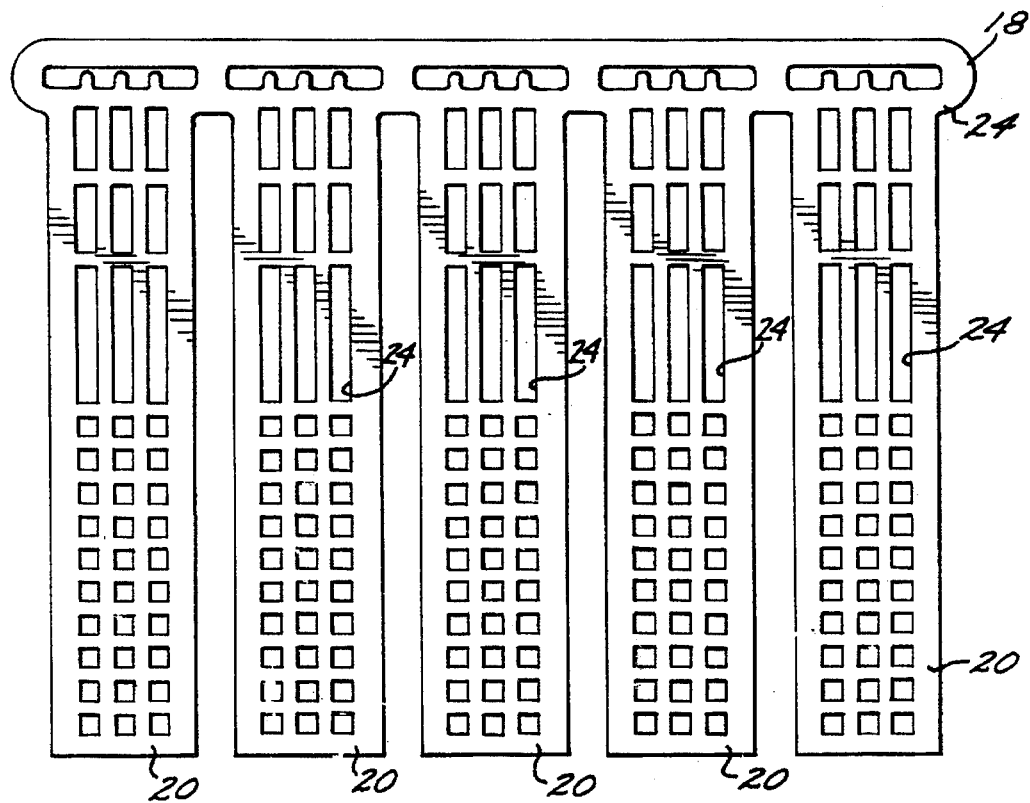
FIG. 2 is a top plan view of a $CO_2$ laser cutting pattern on a plurality of reinforcement members with a polymer coating for cutting the excess polymer from the coated reinforcement members of FIG. 1.
Figure 3:
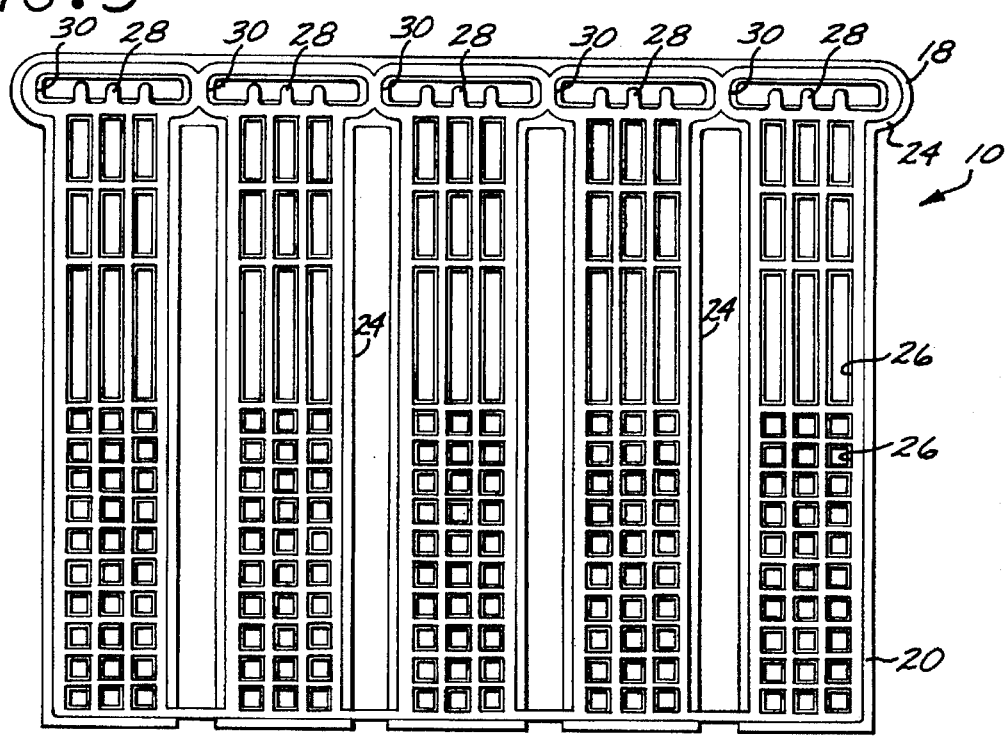
FIG. 3 is a top plan view of the plurality of metal reinforced polymer stents trimmed of excess polymer.
Figure 5:
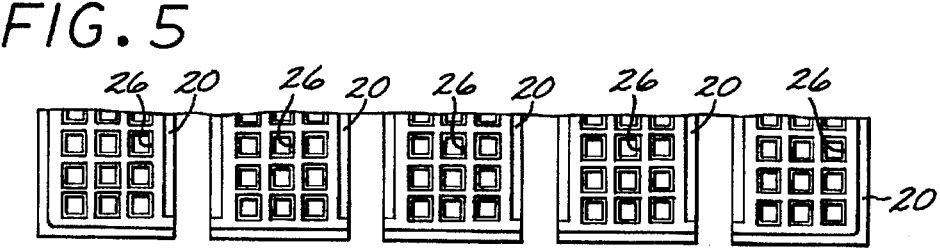
FIG. 5 is a partial top plan view of a the tail ends of a plurality of the metal reinforced polymer stents with the connecting tabs cut, prior to rolling of the stent onto a mandrel.
Figure 4:
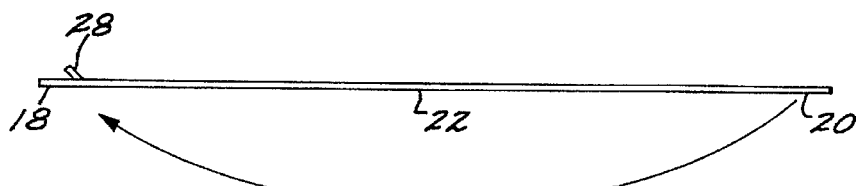
FIG. 4 is a side elevational view of the plurality of metal reinforced polymer stents of FIG. 3 with the teeth bent at 45° out of plane.

While stents are typically formed from biocompatible metals to provide sufficient strength to function as a stent, and a minimal thickness so as to minimize blood flow blockage, such stents can cause complications such as thrombosis, and can cause neointimal hyperplasia, such as by inducement of smooth muscle cell proliferation at the site of implantation of the stent. Such stents also do not provide for the delivery of localized therapeutic pharmacological treatment of a blood vessel at the location being treated with the stent, which can be useful for overcoming such problems. Polymeric films capable of drug delivery do not generally have sufficient strength to function as a stent to maintain luminal patency in and of themselves. It would therefore be desirable to form a stent of materials that provide sufficient radial strength to serve as a stent, and that are capable of absorbing therapeutic drugs and releasing them at a predictable rate for an ascertainable period of time in a blood vessel.

As is illustrated in the drawings, the invention accordingly provides for a metal reinforced polymer stent 10 for use in maintaining the patency of blood vessels, comprising an inner reinforcement member 12 having first and second side surfaces, the inner reinforcement member having a first or head end 18 and a second or tail end 20 and a main body portion 22 between the first and second ends. The reinforcement member is formed so as to be capable of being rolled up into a cylindrical configuration whereby the first end overlaps the second end. The reinforcement member is preferably coated on at least one of the side surfaces with at least one layer of a polymer 24 capable of absorbing and releasing therapeutic drugs. The polymer is preferably biodegradable and bioabsorbable, but can alternatively not be degradable or absorbable. As used in this description, the terms biodegradable, bioabsorbable, reabsorbable, degradable, and absorbable are meant to encompass materials that are broken down and gradually absorbed or eliminated by the body, whether these processes are due to hydrolysis or metabolic processes.

The inner reinforcement member is preferably formed from a thin sheet of a metal selected from the group consisting of stainless steel, platinum-iridium alloy, molybdenum-rhenium alloy, tantalum, gold, combinations thereof, and the like, although other similar materials may also be suitable. The metal sheet is typically approximately 0.001 inches thick, for example. The metal reinforcement member comprises the main structural component of the stent, and provides the principal necessary physical characteristics for the stent. This enables the stent to maintain the required radial strength for the blood vessel in which it is implanted, and provides the desired flexural characteristics to the stent to allow it to be moved into position and expanded.

Figure 6:
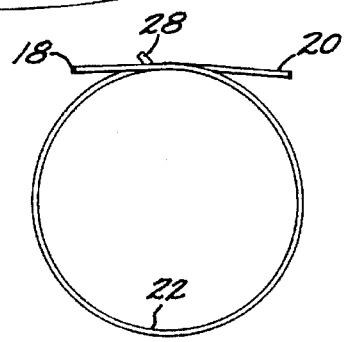
FIG. 6 is a side view of a metal reinforced polymer stent structure of the invention in a rolled configuration, with the teeth directed outwardly.

The sheet of thin metal is preferably cut in the desired shape to form the inner metal stent member with a laser, such as a continuous $CO_2$ laser, a pulsed YAG laser, or an excimer laser, for example, or alternatively, by chemical etching or stamping. The thin metal sheet is preferably cut in a shape that can be used as a stent, such as the shape illustrated in FIG. 1, so that the ends of the stent can be joined to form a contractible, expandable loop, as shown in FIG. 6. The finished stent thus preferably includes a widened head end 18, a tail end 20, and a main body portion 22 between the head and tail ends. The tail and main body portions also preferably include a plurality of apertures 26 to facilitate the process of degradation and absorption of the stent once it is implanted, and to interlock with teeth 28 provided in a slot 30 of the head end. The apertures also allow blood flow through the stent to side branch vessels, and for blood flow to the vessel wall. The tail end and main body portion are thus insertable through the slot so as to form a cylindrically, loop shaped stent that can be furled and contracted for placement within a blood vessel. The stent can be placed in a blood vessel in a furled, cylindrical, contracted loop configuration with a sufficiently small outer diameter so as to be transportable through the targeted blood vessel or other lumen, and of a sufficiently large internal diameter to receive an inflation balloon device (not shown) therein. The stent can thus be urged into an unfurled, expanded configuration by inflation of the inflation balloon device, and locked in the desired expanded configuration by the locking of the teeth in the apertures in the tail and main body portion so that the stent cannot recontract.

The inner stent member is also preferably laminated with a biodegradable, bioabsorbable polymeric film that is capable of absorbing and releasing therapeutic drugs, preferably selected from the group consisting of poly-DL-lactic acid (DL-PLA) and poly-L-lactic acid (L-PLA), although other biodegradable, bioabsorbable polymers such as polyorthoesters, polyiminocarbonates, aliphatic polycarbonates, and polyphosphazenes may also be suitable, and other non-degradable polymers capable of carrying and delivering therapeutic drugs may also be suitable. The thin polymeric films with which the stent is coated are preferably first intermixed with the drug or drugs to be delivered, and then are typically solvent cast or laminated to the surface of the metal stent.

The layers of biodegradable polymeric film on either side of the inner stent member are selected for their ability to absorb and release drugs at predictable rates when the stent is implanted in a blood vessel or other lumen in the body. The biodegradable polymeric film layers can contain the same or different drugs, or combinations of drugs. Alternatively, only one drug releasing layer may be applied to the surface of the inner stent member, or additional layers of biodegradable polymeric film can be built up on top of one another for sequential release of drugs absorbed within them.

The dimensions of the stent as well as its ultimate strength and physical characteristics, in addition to the particular drugs and drug delivery rates are selected for the particular application of the stent. For example, it would desirable for stents according to the principles of the invention to be implanted in coronary arteries to release drugs that can control thrombosis from the inner layer of the stent which is exposed to the bloodstream. Appropriate drugs for this purpose include heparin and prostacyclin. The film layer to be used as the outer layer of the stent can also be provided with drugs such as angiopeptin, methotrexate, and heparin, to control restenosis.

The invention also provides for a method of making a stent for use in maintaining the patency of blood vessels. Initially, the method of the invention provides for cutting a thin planar sheet of metal in a shape to form a plurality of metal reinforcement members connected directly at their head ends, and connected at their tail ends by interconnecting tabs. Each metal reinforcement member is formed to include head and tail ends, a main body portion between the head and tail ends, a slot in the head end for receiving the tail end and the main body portion, and teeth defined in the slot of the head end for engaging the tail end and main body portion within the slot. The sheet of thin metal is preferably cut in the desired shape to form the metal reinforcement member with a laser, such as a continuous $CO_2$ laser, a pulsed YAG laser, or an excimer laser, for example. The metal reinforcement structures can also be cut by other methods known in the art, such as by chemical etching, or stamping. The connecting tabs typically join the tail ends of the metal reinforcement members, and are retained during much of the manufacturing process to help maintain the proper orientation of the tail ends of the metal reinforcement structures.

Following the formation of the metal reinforcement members, the reinforcement members are then preferably laminated with polymer films on each side, with at least one coating of a polymer film. Alternatively, the metal reinforcement structure can also be coated on one side, if desired. At least one laminating polymeric film capable of absorbing and releasing therapeutic drugs is placed on at least one side of the reinforcement member, and the laminating polymeric film is heated to bond the laminating polymeric film to the surface of the inner stent member to form a laminated stent member. Alternatively the polymeric film can be applied by solvent casting, or by adhering the film to the surface of the inner stent member with a biocompatible adhesive. Any excess polymer extending beyond the desired inner edges of the orifices or along the outside edges of the tail and main body portions of the reinforcement structure is then preferably removed, typically by laser cutting, although the excess polymer can also be removed by stamping. The teeth in the slotted portion of the head end of the joined stent structures are then preferably bent to extend about 45° out of the plane of the stent, preparatory to inserting the tail and main body portions into the slotted head portion. The tabs joining the individual stent structures are then preferably cut and removed, such as by a laser, and the tail end is inserted into the slotted head portion. The stents are rolled onto a mandrel (not shown) into a cylindrical configuration with the head end overlapping the tail end, with the teeth extending outwardly at about a 45° angle relative to a tangent to the rolled surface of the stent for engagement of a vessel wall, ready for expansion and implantation.

It has thus been demonstrated that the invention provides for a stent laminated with a thin film of polymeric material capable of absorbing and releasing therapeutic drugs to be released within the affected blood vessel upon implantation. It should be readily apparent that a stent according to the principles of the invention can also be utilized to treat other conditions of vessels or lumens within the body, such as prostate cancer, for example, in which a stent can be placed within the urethra, and a chemotherapeutic drug can be released directly into the urethra.

It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of making a stent for use in maintaining the patency of blood vessels, comprising the steps of:

cutting a thin planar sheet of metal in a shape to form a plurality of reinforcement members, each of said reinforcement members including first and second ends, a main body portion between the first and second ends, said first ends being directly connected together and interconnecting tabs joining the second ends, the first end having a surface defining a slot for receiving the second end and the main body portion, the second end and the main body portion being formed to be insertable through said slot so as to form a loop, and means in said slot for releasably engaging the second end and the main body portion;

placing at least one laminating polymeric film capable of absorbing and releasing therapeutic drugs on at least one side of said plurality of reinforcement members;

heating said laminating polymeric film to bond the laminating polymeric film to the surface of the reinforcement members to form a plurality of laminated reinforcement members;

removing said interconnecting tabs; and rolling said plurality of laminated reinforcement members into a cylindrical configuration whereby the first end overlaps the second end.

2. The method of claim 1, wherein said first end extends in a plane, and said means in said slot comprises a plurality of teeth, and further including the step of bending said teeth to extend approximately 45° out of the plane of the first end prior to said step of rolling said laminated reinforcement members.

3. The method of claim 1, wherein said step of cutting includes cutting the second end and main body portion of each reinforcement member to define apertures therein.

4. The method of claim 3, further including the step of removing excess polymer in the apertures of the second end and main body portion of each reinforcement member.

5. The method of claim 1, wherein said step of cutting the thin planar sheet of metal comprises cutting the thin planar sheet of metal with a laser.

* * * * *